(12) United States Patent
Magagnoli

(10) Patent No.: US 10,492,914 B2
(45) Date of Patent: Dec. 3, 2019

(54) METHOD OF MAKING A SPACER DEVICE HAVING A CONTAINMENT BODY

(71) Applicant: Augusto Magagnoli, Bologna (IT)

(72) Inventor: Augusto Magagnoli, Bologna (IT)

(73) Assignee: Cossington Limited, Kingston upon Thames, Surrey (GB)

(*) Notice: Subject to any disclaimer, the term of this patent is extended or adjusted under 35 U.S.C. 154(b) by 286 days.

(21) Appl. No.: 15/360,789

(22) Filed: Nov. 23, 2016

(65) Prior Publication Data
US 2017/0071745 A1    Mar. 16, 2017

Related U.S. Application Data

(63) Continuation of application No. 14/701,398, filed on Apr. 30, 2015.

(30) Foreign Application Priority Data

Feb. 16, 2015 (IT) .................. BO2015A000065

(51) Int. Cl.
| | | |
|---|---|---|
| *A61F 2/30* | (2006.01) | |
| *A61F 2/38* | (2006.01) | |
| *A61F 2/36* | (2006.01) | |
| *A61F 2/28* | (2006.01) | |
| *A61F 2/40* | (2006.01) | |
| *A61F 2/46* | (2006.01) | |
| *B22F 3/105* | (2006.01) | |
| *B22F 5/00* | (2006.01) | |
| *B28B 1/24* | (2006.01) | |
| *B29C 45/00* | (2006.01) | |

(Continued)

(52) U.S. Cl.
CPC ............. *A61F 2/3094* (2013.01); *A61F 2/28* (2013.01); *A61F 2/36* (2013.01); *A61F 2/3859* (2013.01); *A61F 2/40* (2013.01); *A61F 2/4684* (2013.01); *B22F 3/1055* (2013.01); *B22F 5/00* (2013.01); *B28B 1/24* (2013.01); *B29C 45/0013* (2013.01); *A61F 2002/2835* (2013.01); *A61F 2002/3092* (2013.01); *A61F 2002/30672* (2013.01); *A61F 2002/30677* (2013.01); *B29K 2105/16* (2013.01); *B29K 2995/0056* (2013.01); *B29L 2031/7532* (2013.01)

(58) Field of Classification Search
CPC . B22F 3/1055; B22F 5/00; B28B 1/24; B29C 45/0013; B29L 2031/7532; B29K 2995/0056; B29K 2105/16
See application file for complete search history.

(56) References Cited

U.S. PATENT DOCUMENTS

| | | | | |
|---|---|---|---|---|
| 4,593,685 A | * | 6/1986 | McKay ............. | A61B 17/8808 606/92 |
| 4,919,666 A | * | 4/1990 | Buchhorn ............. | A61F 2/30 606/62 |

(Continued)

*Primary Examiner* — Jacob J Cigna
(74) *Attorney, Agent, or Firm* — Themis Law

(57) ABSTRACT

A method of making a spacer device or a device to be implanted in a human body that includes a containment body and is suitable for treating a bone seat or a joint seat of the human body includes a base portion and side walls that extend from the base portion and that delimit between them at least one cavity, wherein the containment body has a plurality of pores and/or at least one opening, configured to place the at least one internal cavity in communication with the outside of the containment body.

14 Claims, 4 Drawing Sheets

(51) Int. Cl.
*B29K 105/16* (2006.01)
*B29L 31/00* (2006.01)

(56) References Cited

U.S. PATENT DOCUMENTS

| | | | | |
|---|---|---|---|---|
| 5,123,927 A * | 6/1992 | Duncan | ............... | A61F 2/30942 623/20.21 |
| 6,179,876 B1 * | 1/2001 | Stamper | ............. | A61B 17/8808 623/16.11 |
| 6,355,067 B1 * | 3/2002 | Bloebaum | .......... | A61B 17/1604 606/92 |
| 6,979,336 B2 * | 12/2005 | Durniak | ............. | A61B 17/8802 606/92 |
| 7,780,674 B2 * | 8/2010 | Medley | ............. | A61B 17/8802 606/60 |
| 7,824,699 B2 * | 11/2010 | Ralph | ................... | A61K 9/0024 424/422 |
| 8,080,059 B2 * | 12/2011 | Fell | .................... | A61F 2/30767 623/14.12 |
| 9,616,205 B2 * | 4/2017 | Nebosky | ................ | A61B 17/56 |
| 9,839,523 B1 * | 12/2017 | Foran | ................... | A61F 2/30771 |
| 2005/0012610 A1 * | 1/2005 | Liao | .................... | A61B 5/0008 340/539.12 |
| 2005/0260247 A1 * | 11/2005 | Ralph | ................... | A61K 9/0024 424/423 |
| 2009/0012615 A1 * | 1/2009 | Fell | .................... | A61F 2/30767 623/14.12 |
| 2012/0165871 A1 * | 6/2012 | Malone | ............. | A61B 17/7064 606/247 |
| 2012/0256344 A1 * | 10/2012 | Stolarski | ............. | A61F 2/30942 264/251 |
| 2013/0197530 A1 * | 8/2013 | McKay | ................ | A61F 2/2846 606/94 |

* cited by examiner

METHOD OF MAKING A SPACER DEVICE HAVING A CONTAINMENT BODY

FIELD OF THE INVENTION

The present invention relates to a method of making a temporary and/or disposable spacer device for the treatment of an infected bone seat or joint seat that comprises a containment body.

In particular, the aforementioned containment body constitutes, after the temporary and/or disposable spacer device has been made, an integral part of the spacer device itself.

BACKGROUND OF THE INVENTION

It is known that prostheses implanted inside the human body can be subject to infections.

When this occurs, the infected prosthesis must be removed from the implantation site and, before implanting another prosthesis, it is necessary for the infection to be eradicated.

During such a step, spacer devices are normally used in order to keep the shape of the bone seat or of the joint seat in which the new prosthesis will be implanted substantially unchanged.

Such a procedure is known as "two-step treatment" for the removal of an infected prosthesis and the implantation of a new prosthesis.

Such spacer devices do, however, have some limitations in terms of the amount or type of pharmaceutical or medical substance that can be released or, furthermore, in terms of the possibility of ensuring substantially uniform release of such a substance. Furthermore, it should be observed that in the case in which a spacer device has only the outer surface porous, the amount of pharmaceutical or medical substance that can be impregnated in the spacer device is limited by the depth and by the extension of the porous surface itself. In this case, the spacer device could not be able to ensure the release of the pharmaceutical or medical substance for a period equal to that necessary to completely heal the infected site.

Finally, there are spacer devices that are made from a biocompatible material that has pores for the entire volume occupied by the device itself.

Such spacers are, however, usually preloaded with a given antibiotic or with a given medical or pharmaceutical substance and, therefore, the surgeon does not have the freedom to choose which drug to use, hence being unable to adapt the drug itself to the patient's real needs.

Therefore, there is a need to have a spacer device that ensures uniform and constant release of the pharmaceutical or medical substance present through the entire outer surface of the spacer device itself, even for prolonged periods.

There are also preformed spacer devices that are produced by casting antibiotic-loaded bone cement in a mold until it sets, removing the mold and extracting the set spacer device, which is then processed or finished according to requirements.

Alternatively, the surgeon can make a spacer himself during the operation, using molds, usually made from silicone of suitable geometry, which are filled with antibiotic-loaded bone cement, to which a further antibiotic different from the first is optionally added. Once polymerization has taken place, the surgeon extracts the spacer from the silicone mold, facilitated by the flexible nature of this material, and then proceeds with the implanting, also in this case possibly finishing the spacer if necessary.

Therefore, there is a need for the surgeon to be able to choose the pharmaceutical or medical substance to be applied to the spacer device itself, so as to meet the specific needs of the patient.

At the same time, this possibility is associated with the need to have, in any case, a temporary and/or disposable spacer device of predetermined and correct shape and size, without the risk of the surgeon, having to make the spacer device directly in situ, being able to obtain a shape that is irregular or incompatible with the actual anatomical requirements of the patient, or in any case to be finished and processed before implanting.

SUMMARY OF THE INVENTION

The task of the present invention is to improve the state of the art.

In such a technical task a purpose of the present invention is to form a temporary and/or disposable spacer device for the substantially uniform release of at least one pharmaceutical or medical substance in a bone seat or joint seat to be treated that comprises a containment body.

Another purpose of the present invention is to form a temporary and/or disposable spacer device, the configuration of which substantially corresponds to that of the infected bone seat or joint seat to be treated or part of it.

A further purpose of the present invention is to form a temporary and/or disposable spacer device, which has a high mechanical resistance to the stresses to which it is subjected during use. In particular, when the containment body is provided for making a spacer device subjected to rubbing, like in the case of a joint of the human body, it must be made from a material with a high resistance to abrasion.

Such a spacer device is configured for releasing a pharmaceutical or medical substance in a substantially uniform manner through the entire outer surface of the spacer device itself.

Moreover, such a spacer device can be made such that the release of such a pharmaceutical or medical substance is ensured also for long periods.

In accordance with a further aspect of the present invention, a method of making a spacer device, for the treatment of a bone seat or joint seat, comprising a containment body, is foreseen, as described hereinafter.

The dependent claims refer to preferred and advantageous embodiments of the invention.

BRIEF DESCRIPTION OF THE DRAWINGS

Further characteristics and advantages of the present invention will become clearer from the detailed description of a preferred but not exclusive embodiment of a containment body for forming a spacer device, illustrated for exemplary but not limiting purposes in the enclosed drawings, in which.

DETAILED DESCRIPTION OF EMBODIMENTS OF THE INVENTION

Figure 1:
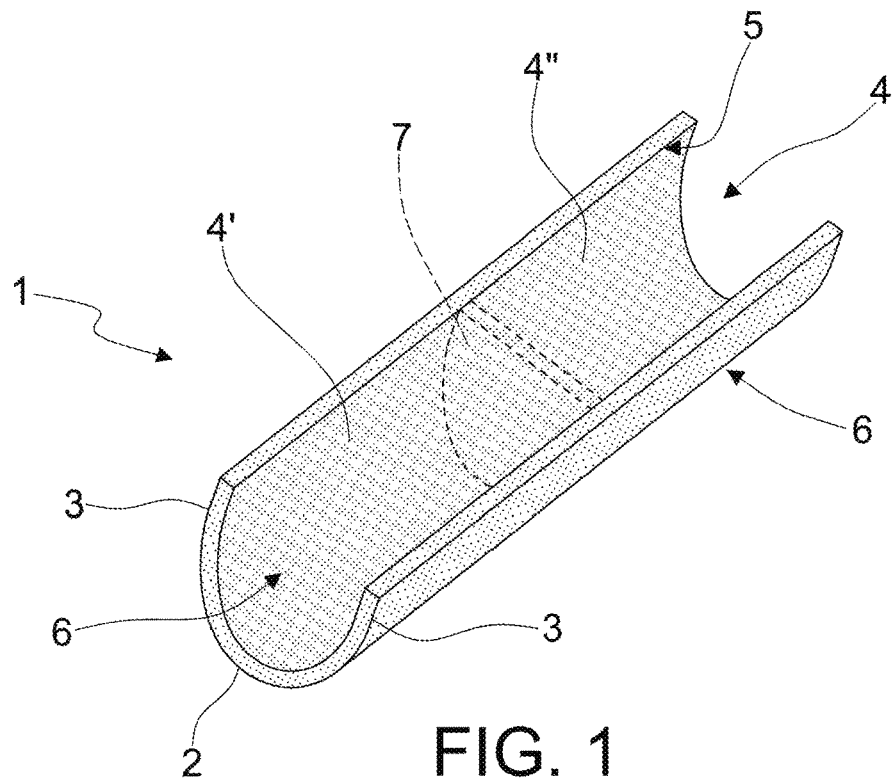
FIG. 1 is a schematic perspective view from above of a containment body according to the present invention.

With reference to the enclosed figures, a containment body for forming a spacer device, for example a temporary and/or disposable spacer device, is indicated in its entirety with 1.

More specifically, the containment body 1 is foreseen for making or forming a spacer device to be implanted in a bone seat or joint seat of the human body, typically replacing an infected prosthesis.

Such a spacer device is defined as "temporary" in the sense that, once its function of healing and maintaining the space of the bone seat or joint seat has been carried out, it will be removed from the concerned area and replaced for example with a permanent prosthesis.

In this regard, the spacer device carries out the function of maintaining the joint spaces as well of healing the bone infection by freeing an amount of antibiotic in the infected area. As far as this last aspect is concerned, the spacer manages to heal the infection in progress by releasing antibiotic in a targeted fashion and in infinitesimal quantity, whereas the application of even high doses of antibiotic, but with methods that do not provide for the use of spacers, like for example washing of the infected area with high-dosage antibiotic solutions, does not allow the same results to be obtained.

Studies carried out in this field have indeed found that the bone tissue absorbs in a concentrated manner all of the antibiotic molecules (even if they are few) freed daily by the spacer. This of course happens if the antibiotic is released by the spacer in contact with or adjacent to the bone tissue, in which case the amount of antibiotic locally reaches the effective concentration to eradicate the infection. For this reason it is essential for the spacer to extend for the entire area of the infection, by this meaning that if the infected prosthesis is a long prosthesis then a long spacer will be used and in the case in which the infected prosthesis is short then a short spacer will be used. In the case in which a short spacer is placed where before a long prosthesis was implanted, part of the bone would not be treated with antibiotic, in such a way leaving bacteria free to multiply.

The containment body 1 has a configuration such as to be able to couple, in a substantially complementary manner, with the bone seat or joint seat to which it must be constrained.

The containment body 1 is in the form of a substantially hollow casing provided with at least one opening through which to introduce a filling material, preferably solidifiable, in order to make a spacer device. Basically, the containment body 1 corresponds to the hollow figure—acting as a sort of mold—of the spacer device to be made (once the body itself has been filled with a viscous, liquid or fluid material, possibly of the type that becomes solid or solidifiable) and, in particular, constitutes the outer portion thereof.

Such a temporary and/or disposable spacer device, once formed, thus comprises an outer portion, corresponding to the containment body 1, and an inner portion, comprising the filling material and, possibly, a core or reinforcing structure, as described better hereafter.

The aforementioned temporary and disposable spacer device also constitutes the object of the present invention.

The attached figures illustrate, purely as non-limiting examples, some possible configurations of a containment body according to the present invention.

Figure 2:
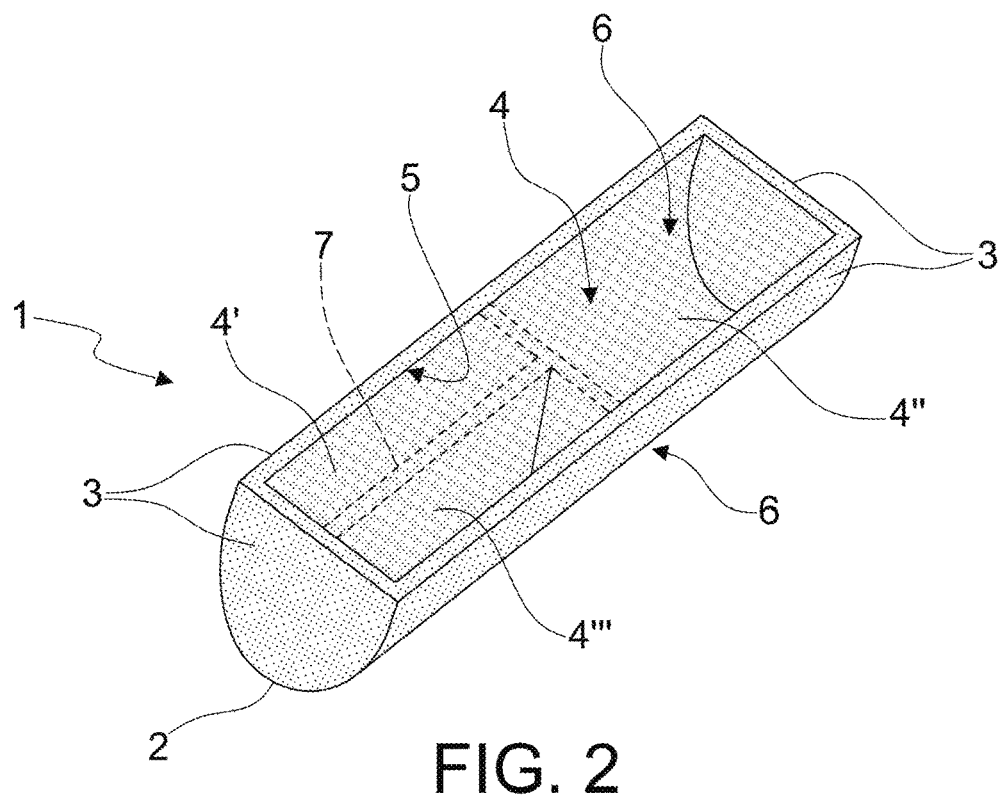
FIG. 2 is a schematic perspective view from above of another version of the containment body according to the present invention.
Figure 3:
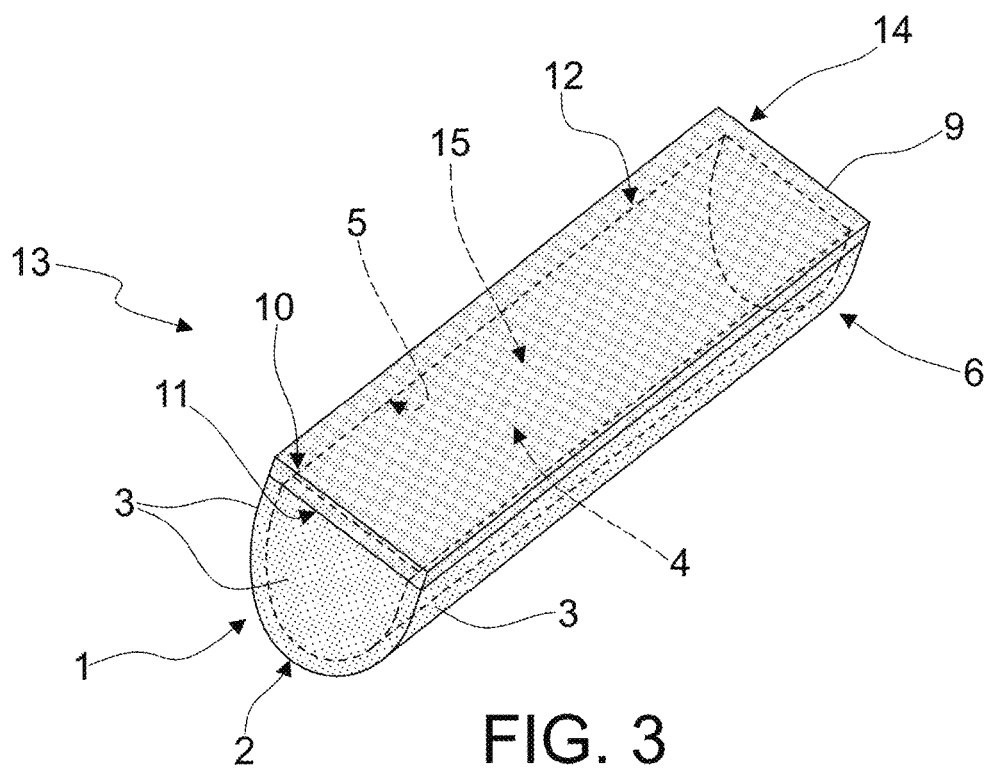
FIG. 3 is a schematic perspective view from above of the containment body according to FIG. 2 associated with a further component.

In greater detail, as an example, the attached FIGS. 1-3 schematically show some possible basic configurations of the containment body according to the present invention, in which the containment body itself has a substantially elongated configuration.

Figure 4:
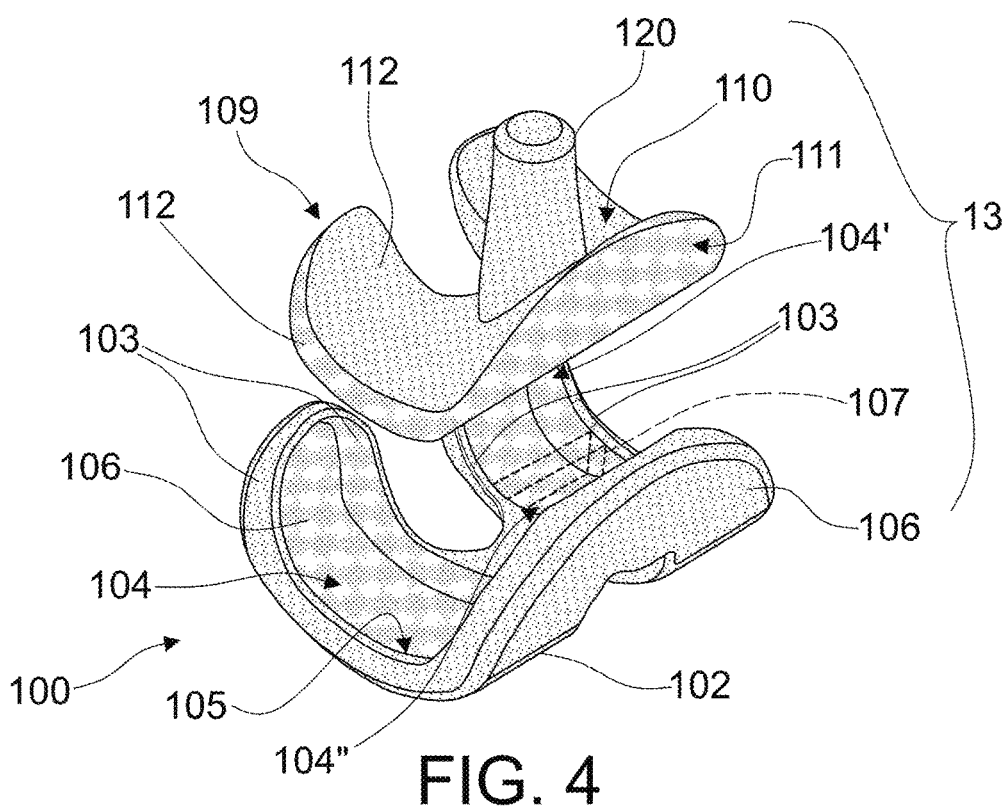
FIG. 4 is an exploded view of a temporary and disposable spacer device comprising a containment body according to the present invention associated with a further component.

A further version of a containment body according to the present invention, foreseen for making a temporary and disposable spacer device able to be constrained to the femoral end of the knee is illustrated in FIG. 4.

Figure 5:
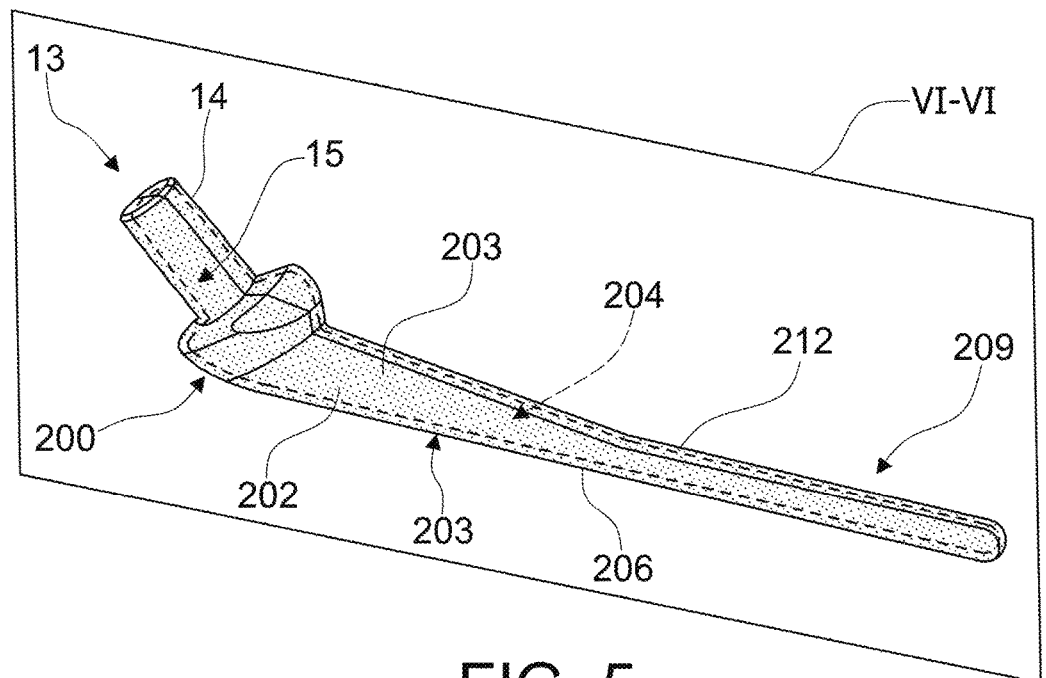
FIG. 5 is a perspective view of a further configuration of a temporary and/or disposable spacer device comprising a containment body according to the present invention.
Figure 6:
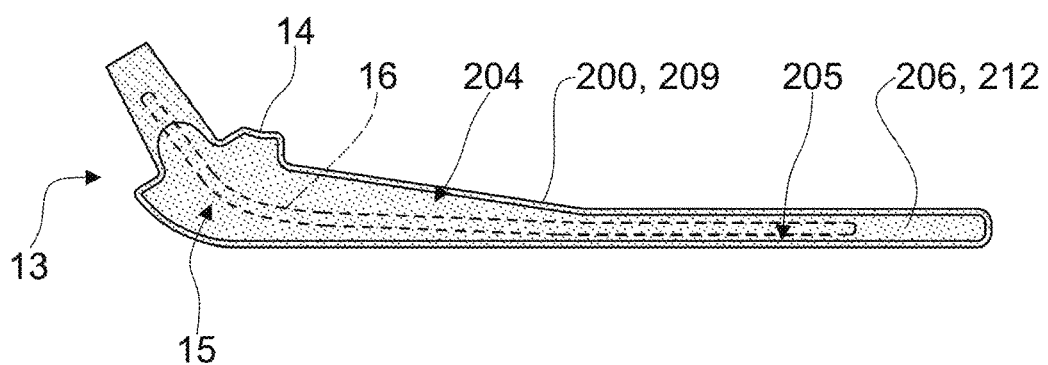
FIG. 6 is a section view, along a plane line VI-VI, of the temporary and/or disposable spacer device according to FIG. 5.

FIGS. 5 and 6, on the other hand, depict a further version of a containment body according to the present invention, foreseen for making a temporary and disposable spacer device for the shoulder or hip joint.

However, further configurations of the containment body according to the present invention are possible, to make spacer devices shaped differently with respect to what is illustrated in the attached figures, without any limitation.

The containment body 1 for making a temporary and/or disposable spacer device comprises a base portion 2 and side walls 3 that extend from the base portion 2.

In particular, the base portion 2 and the side walls 3 delimit a cavity 4 between them.

In the latter it is possible to house at least one filling material, possibly of the solidifiable type.

The base portion 2, as well as the side walls 3, can be made in various thicknesses. Such thicknesses can be selected as a function of specific requirements of use such as the shape of the spacer device that it is intended to make or the structural strength that it must ensure. As it can be seen, e.g. in FIGS. 2 and 3, the cavity defined by base portion 2 and side walls 3 has a height, a width, and a depth smaller than at least one of the height or the width of containment body 1 and further has an open face defined by the height and the width of containment body 1.

According to a version of the present invention, the thickness of the base portion 2 and of the side walls can be comprised between 0.5 mm and 20 mm, preferably from 0.5 to 4 mm.

The containment body 1 can, however, be made with different thicknesses with respect to those indicated above, without for this reason departing from the scope of protection of the present invention.

As stated, the containment body 1 can have an opening 5 for access to the cavity 4. Such an opening 5 is delimited by the side walls 3, in particular by their outer peripheral edges.

The opening 5, in one version of the invention, is opposite the base portion 2.

Through the opening 5 it is possible to introduce at least one filling material inside the containment body 1.

According to a version of the present invention, the side walls 3 extend perimetrically from the base portion (see FIGS. 2 and 3).

In accordance with such a version, the side walls 3 are continuous to one another, laterally delimiting the cavity 4 and, consequently, the opening 5.

The containment body 1 according to the present invention, and more specifically its base portion 2 and the side walls 3, is made from a biologically compatible material.

According to a version of the present invention, the containment body 1 is made from a porous material, as described more clearly hereafter.

The biologically compatible material constituting the containment body 1 can be selected among plastic and/or polymeric materials, such as polymethylmethacrylate (PMMA), polyethylene (PE), polyvinylchloride (PVC), polystyrene (PS), polyether ether ketone (PEEK), ultra high molecular weight polyethylene (UHMWPE), high or low density polyethylene, etc., or non-polymeric materials, ceramics, metals, metal alloys, organometallic compounds, and/or a combination thereof.

With reference to biocompatible plastic materials, the preferable ones are those that are sufficiently rigid at a temperature of about 36° C., i.e. body temperature, at the same time ensuring the mechanical performance necessary according to the present invention and described in the present description.

Specifically, the aforementioned plastic materials can be selected among thermoplastic polymers, such as acrylic resins, polyethylene, polypropylene, polyester, etc., thermoformable polymers, and other similar materials.

In a version of the present invention, the biologically compatible material is a bone cement based on polymethylmethacrylate (PMMA). PMMA has the advantage of welding perfectly with the filling material that, at least in one version of the invention, is bone cement also comprising PMMA undergoing polymerization.

In a version of the invention, the aforementioned biologically compatible material is initially without pharmaceutical or medical substances.

In a second version, the aforementioned biologically compatible material initially comprises at least one pharmaceutical or medical substance.

On the other hand, as far as the filling material is concerned, typically it can be bone cement.

The filling material can, in a further version of the invention, comprise an inorganic hydraulic cement or a biocompatible solid filling material.

According to a further version of the present invention the filling material can be a ceramic cement, like for example calcium sulfate known as gypsum or $CaSO_4$, which as well as solidifying in short time periods is able to release calcium ions.

According to another version, the filling material could be based on complex ceramic cements based on Silicates and Calcium Aluminates.

According to a further version, the filling material can be a liquid or a fluid the viscosity of which is selected as a function of the duration of the period necessary for the treatment of the infected site, as described better hereafter.

For example, the liquid or the fluid could be able to be eluted through the containment body (or even through the closing body) for a time period that can vary between 1 and 12 months.

However, it is possible to use further biocompatible filling materials, with respect to what is described above, without for this reason departing from the scope of protection of the present invention.

In a version of the invention, the filling material, which can be prepared by the surgeon during the operating procedure, lacks any pharmaceutical or medical substances and can have them added to it based on the choice of the surgeon and the patient's needs.

In a further version of the invention, the aforementioned filling material can comprise at least one pharmaceutical or medical substance already arranged in the material that constitutes the filling material itself, and optionally it can, in the preparation step, be added to with a further substance.

The filling material, by virtue of the preparation and solidification step to which it is subjected, is porous.

As stated, according to a version of the present invention the containment body 1 is porous, since it has pores 6.

In a version of the invention, the pores 6 can be interconnected with each other and/or homogeneously distributed in the entire volume of the containment body 1 and, therefore, through its base portion 2 and its side walls 3.

As described better hereafter, the pores 6 place the at least one cavity 4 in communication with the outside of the containment body 1.

Therefore, in the case in which the pharmaceutical or medical substance is arranged inside the at least one cavity 4 of the containment body 1—in the filling material—the pores 6 promote the release thereof also through the containment body 1 itself.

According to an aspect of the present invention, the size of the pores 6 is such as to prevent the occurrence, during use, of bone growth inside the containment body 1 and, therefore, inside the temporary and/or disposable spacer device that comprises it.

Such a configuration of the pores 6, therefore, facilitates the subsequent removal of the spacer device from the bone seat or joint seat treated, once its healing function has been carried out.

As an example, the pores 6 can, in one version, have dimensions on average smaller than 100 microns.

According to a further version of the present invention, the containment body 1 can have a plurality of through openings, not illustrated in the figures, suitable for placing the inside of the at least one cavity 4 in communication with the outside of the containment body 1 itself.

Similarly to what has been described above, in one version of the invention, such through openings can have dimensions such as not to allow bone growth through the portions of the containment body 1.

The through openings can have a circular cross section or any other geometry suitable for the purpose.

According to another version of the present invention, the containment body 1 can be porous, and thus comprise pores 6, and also have a plurality of through openings, with the same aims described for the previous versions.

According to a version of the present invention, the containment body 1 can comprise at least one separating wall 7, represented in the attached figures with a broken line, positioned inside the at least one cavity 4 in order to divide the latter into several portions separated from one another.

So, the at least one separating wall 7 defines spaces 4', 4" inside the at least one cavity 4 separated from one another, for housing respective filling materials, possibly different from one another.

This possibility is particularly advantageous in the case in which a surgeon intends to use different types of pharmaceutical or medical substances for the treatment of specific portions of the bone seat or joint seat.

The at least one separating wall 7 rises up from the base portion 2 and/or from at least one of the side walls 3.

In a version, the containment body 1 can comprise at least one separating wall 7 that defines, inside the at least one cavity 4, two portions 4', 4" that are distinct from each other (see FIG. 1).

In a further version, the at least one separating wall 7 defines, inside the at least one cavity 4, three portions 4', 4", 4''' that are distinct from each other (see FIG. 2).

Further versions are possible comprising a greater number of separating walls 7, possibly configured differently with respect to what is illustrated in the attached figures, without for this reason departing from the scope of protection of the present invention.

Concerning this, according to a further version of the present invention, the containment body 1 comprises a plurality of separating walls 7 interconnected to one another to constitute a substantially trabecular structure, comprising a plurality of cavities.

Such a substantially trabecular structure can be filled or impregnated with at least one pharmaceutical or medical substance.

With reference to such a version, and as already stated, the containment body 1 in a version of the invention is porous and thus has a plurality of pores 6 suitable for placing the cavities present in the trabecular structure in communication with the outside of the containment body 1.

According to a further version of the present invention, the containment body 1 can have a plurality of through openings through the side walls 3 and/or the base portion 2, thus placing the cavities present in the trabecular structure in communication with the outside of the containment body 1 itself.

According to another version, the containment body 1 can be porous and have a plurality of through openings suitable for placing the cavities of the trabecular structure in communication with the outside of the containment body 1.

According to a version of the invention, the at least one separating wall 7 is made from the same material from which the containment body 1 is made.

According to an aspect of the present invention, the containment body 1 can be associated with a closing body 9, for closing the access opening 5 to the at least one cavity 4 (FIGS. 3-5).

In a version of the invention, the closing body 9 has a configuration substantially corresponding to that of the opening 5.

With the containment body 1 and the closing body 9 associated with each other, in practice, a closed casing is obtained that on the outside is configured to substantially match the shape of the bone seat or joint seat to be treated or part thereof. "Substantially" indicates a perfect match with a tolerance of ±20%.

As stated, inside such a closed casing there is at least one cavity 4, which can be filled with the filling material described earlier.

The closing body 9 has a first surface 10 and a second surface 11, opposite one another.

Similarly to what has been described for the containment body 1, the closing body 9 can also be porous.

In greater detail, the closing body 9 can comprise a plurality of pores 12.

In a version of the invention, the pores 12 are interconnected to one another, suitable for placing the first surface 10 in communication with the second surface 11, therefore placing the cavity 4 in communication with the outside of the casing.

The pores 12 of the closing body 9 have substantially the same characteristics as the pores 6 of the containment body 1 described earlier.

The pores 12 are present substantially uniformly in the entire closing body 9; therefore, the release of at least one pharmaceutical or medical substance can also take place through the closing body 9 and, more specifically, through the pores 12 present in it.

According to a further version of the present invention, the closing body 9 can have at least one through opening, of small size, through the first surface 10 and the second surface 11, not illustrated in the figures.

In fact, the at least one through opening determines a path suitable for placing the first surface 10 in communication with the second surface 11.

According to another version of the present invention, the closing body 9 can be porous and have at least one through opening described earlier.

FIG. 4 illustrates a further embodiment of a containment body according to the present invention, indicated with reference numeral 100, foreseen for making a temporary and/or disposable spacer device for the knee joint.

In greater detail, the containment body 100 is foreseen for making a spacer device able to be constrained to the femoral portion of the knee joint.

Hereafter, the same reference numerals will be used to indicate the same components described in the previous embodiment, increased by one hundred.

The containment body 100 differs overall from the previous embodiment only in its shape.

In particular, the containment body 100 comprises a base portion 102 from which side walls 103 extend perimetrically, the side walls 103 being configured so as to match the femoral bone end of the knee, to which it must be constrained. In particular, the base surface 102 corresponds to the surface of the femoral bone that is jointed to the tibial bone end.

The containment body 100 has at least one cavity 104, for housing at least one filling material, preferably of the solidifiable type.

Similarly to what has been described for the previous embodiment, the containment body 100 can have an opening 105, delimited by the side walls 103, in particular by their outer perimeter edges, for access to the at least one cavity 104.

According to a version of the present invention, the containment body 100 can comprise at least one separating wall 107, illustrated with a broken line, to delimit inside the at least one cavity 104 at least two portions 104', 104".

The at least one separating wall 107 can have a different shape with respect to that illustrated in the attached figures, in order to delimit a greater number of spaces in the at least one cavity 104, without any limitation.

According to a version, the containment body 100 can comprise a plurality of separating walls 107 configured so as to define a substantially trabecular structure inside the containment body 100 itself.

A substantially trabecular structure thus defined comprises a plurality of cavities 104 that can be filled or impregnated with at least one filling material.

The containment body 100 can be associated with a closing body 109, suitable for closing the opening 105.

The closing body 109 corresponds to the surface to be constrained to the femoral end of the knee, so as to recreate, together with the containment body 100, the complete femoral end of the knee and allow the articulation with a tibial component or with the tibial bone end of the knee.

In use, the containment body 100 and the closing body 109, coupled together, constitute a closed casing equipped with at least one internal cavity 104 in which it is possible to house at least one filling material, of the solidifiable type.

The containment body 100, just like the closing body 109, can be porous and, in greater detail, can have a plurality of pores, respectively indicated with 106 and 112, suitable for placing the at least one internal cavity 104 in communication with the outside of the containment body 100 and of the closing body 109.

According to an aspect of the present invention, the containment body 100 and/or the closing body 109 can have a connection element 120 that extends from the closing body 109 going away from it.

With reference to the embodiment illustrated in FIG. 4, the connection element 120 extends from the closing body 109 and has a substantially elongated configuration, similar to a pin, and is suitable for being introduced and housed in a site able to be formed at the femoral end to be treated close to the knee joint.

In general, the connection element 120 can nevertheless have any other configuration suitable for promoting the connection of the closing body 109 to an end or to a bone seat, without any limitation.

FIGS. 5 and 6 illustrate a further embodiment of a containment body according to the present invention, wholly indicated with reference numeral 200.

Hereafter, the same components corresponding to those of the embodiments described earlier will be indicated with the same reference numerals increased by one hundred.

The containment body 200 differs overall from the previous embodiments for its configuration.

More specifically, the containment body 200 is configured for making a temporary and/or disposable spacer device for the shoulder or hip joint.

The containment body 200 has a base portion 202 from which side walls 203 extend perimetrically, delimiting at least one cavity 204.

The at least one cavity 204 is accessible from an opening 205 delimited by the side walls 203, in particular by their outer perimeter edges.

Figure 7:
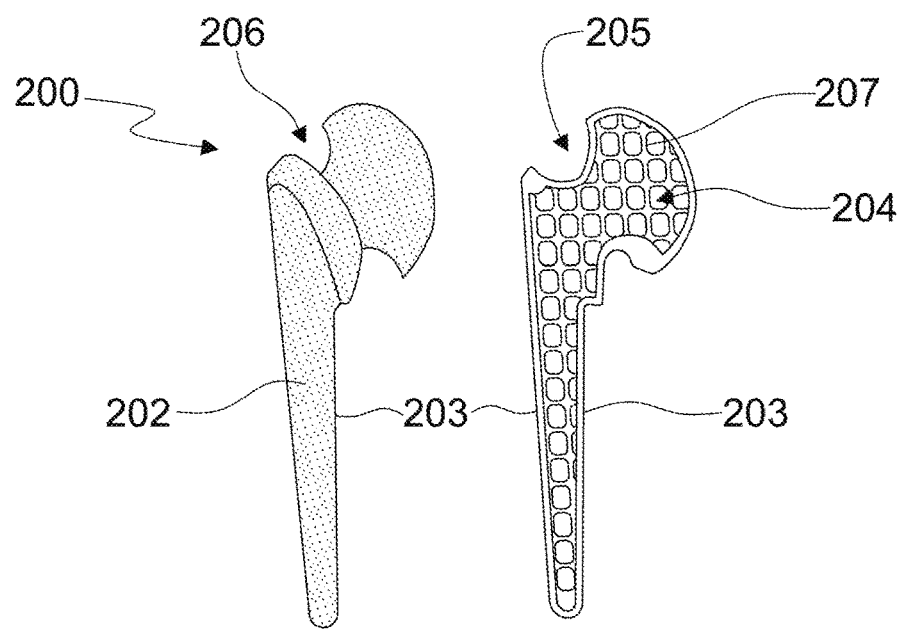
FIG. 7 is a side view of a temporary and/or disposable spacer device according to the present invention sectioned in two halves arranged side-by-side.

The containment body 200 can comprise at least one separating wall 207 (see FIGS. 7 and 8) suitable for delimiting at least one cavity 204 inside the containment body 200.

The containment body 200 can also comprise a plurality of separating walls 207 configured so as to define a substantially trabecular structure, comprising a plurality of cavities 204.

Since the containment body 200 can be porous and/or comprise at least one through opening through the side walls 203 and/or the base portion 202, the at least one cavity 204 is in communication with the outside of the containment body 200.

As described for the previous embodiments, the containment body 200 can be associated with a closing body 209, for closing the access opening 205 to the at least one cavity 204.

In use, the containment body 200 and the closing body 209 associated with one another constitute a closed casing.

Regarding this, it should be observed that in the case in which the spacer device to be made has a plane of symmetry, the containment body and the closing body can be shaped so as to mirror one another.

As an example, the version of the spacer device illustrated in FIG. 5 has a plane of symmetry, wholly indicated with VI-VI.

According to such a version, therefore, the closing body 209 and the containment body 200 are shaped so as to mirror one another.

In the case in which the closing body 9, 109, 209 is foreseen, there can be constraining means (not illustrated in the figures), so as to constrain such a closing body 9, 109, 209 to the respective containment body 1, 100, 200, once the filling of the at least one cavity 4, 104, 204 with the filling material is complete.

Such constraining means can be present in the outer peripheral edges of the containment body 1, 100, 200 and/or in the outer peripheral edges of the closing body 9, 109, 209.

The constraining means can for example comprise matching edges, suitable for inserting in the corresponding edges of the opposite body and for being held by them.

Alternatively, the constraining means can be snap or bayonet constraining means, so as to stably connect the containment body 1, 100, 200 with the closing body 9, 109, 209.

According to an aspect of the present invention, in order to make the device according to the present invention, firstly the shape of the spacer device to be made is set, a hollow figure corresponding to that of the spacer device to be made is generated, a plane, possibly of symmetry or a line, of the spacer device is identified, so as to obtain a containment body, and possibly a closing body, corresponding and congruent to the spacer device to be made.

In this way the geometry or configuration of the containment body and of the possible closing body is established, potentially being able to match any geometry of spacer device or of implantable device for the human body.

The containment body 1, 100, 200, as well as the closing body 9, 109, 209 when present, can be made through a forming process in a mold.

As a non-limiting example, such a process can be a sintering process.

The latter, in short, comprises an initial forming step of a product from a powdered material or a mixture of powdered materials that, initially, are pressed and formed inside a mold.

Thereafter, the pressed component thus formed, also known as green component, is subjected to the sintering step through which the single granules are at least partially fused together, thus determining a compact finished product.

The powdered material to be sintered is generally mixed with solvents or glues or binders that promote the initial forming step thereof (generating a partial gluing of the powders), which are subsequently dispersed during the successive steps of the process.

As an example, the powdered material can have a grain size comprised between 1 and 1000 microns.

The sintering step takes place at high temperature, through dry heat or through steam, leading to an at least partial surface thermal fusion. High pressure, solvent or binder and heat can also be used simultaneously.

Such a powdered material can comprise, for example, materials such as thermoplastic or thermosetting plastics, metals, ceramics, composite materials, and in general materials that are biocompatible and implantable in the human body, therefore without causing rejection by the tissues with which they are placed in contact.

The powdered material can belong to other types of materials with respect to those indicated above, provided that they are of the type that is biocompatible and implantable in the human body without any limitation.

By means of the aforementioned sintering process it is possible to obtain a containment body 1, 100, 200 and/or a closing body 9, 109, 209 that are compact or porous, in this last case comprising a plurality of pores, possibly intercommunicating with each other, such as to place the inside of the at least one cavity 4, 104, 204 in communication with the outside.

According to a further version, the containment body 1, 100, 200 and the closing body 9, 109, 209 when foreseen, can be made through an injection molding process, for example in a press, of a thermoplastic resin, of the type that is biocompatible and implantable in the human body.

In order to give open porosity to the containment body 1, 100, 200 and/or to the closing body 9, 109, 209, it is possible to add additives to the resin itself, like for example inorganic salts or sodium chloride.

As a function of the degree of porosity intended to be given to the containment body 1, 100, 200 and/or to the closing body 9, 109, 209, the additives can be added in variable quantities comprised between 1% and 99%, whereas the remaining part consists of the resin itself; so, as can be understood, the greater the amount of additive added to the resin, the greater the porosity of the manufactured product made.

The latter becomes evident by subjecting the manufactured product to successive baths in suitable solvents, like for example water or steam, removing the additives that therefore leave empty spaces or cavities in the manufactured product itself.

The cavities left by the additives will have the dimensions and the number correlated to the dimensions and the amount of additive itself.

In a further version of the invention, the additives can be solid, liquid, gaseous or mixtures thereof, of the organic or inorganic type.

In this case, the manufactured products produced can be made in series, constrained only to the figure or to the shape that is wished to be obtained.

According to a further version, the containment body 1, 100, 200, as well as the closing body 9, 109, 209 when present, can be made through an additional process like, for example, a three-dimensional printing process of a biocompatible material able to be implanted in the human body, of the type described above or preferably acrylic in nature.

Through the three-dimensional printing process it is possible to obtain a containment body 1, 100, 200, and possibly a closing body 9, 109, 209, of the porous type or having a honeycomb structure and therefore substantially trabecular.

Indeed, the three-dimensional printing process makes it possible to make possible separating walls 7, 107, 207 inside the cavity 4, 104, 204 directly during the forming/molding step of the containment body 1, 100, 200, thus reducing the overall production times.

According to a version of the present invention, the separating walls 7, 107, 207 that can be made through the three-dimensional printing process can be configured so as to define a substantially trabecular structure for the containment body 1, 100, 200.

According to a version of the present invention, in the three-dimensional printing process, for example, it is possible to foresee the use of wire-like materials consisting of thermoplastic resins such as PMMA, PE, PEEK, etc.

However, it is possible to use different materials from those described above, provided that it is of the biocompatible type and implantable in the human body, without for this reason departing from the scope of protection of the present invention.

The honeycomb or trabecular structure, once made, is filled with a filling material that, by solidifying and setting, determines the creation of a spacer device or device to be implanted, having become a single piece with the containment body and the possible closing body.

In this way it is possible to obtain customized or personalized products for each individual patient.

The customized products can thus be made from plastic or metallic materials, for example through laser sintering of metallic powder, etc., also making complex structures that cannot be obtained through an injection press. For example, it is possible to make containment bodies of at least one pharmaceutical or medical substance to be released outside of them, and successive spacers for whatever region of the human body, or furthermore prosthesis for the cranium or prosthesis for the chest (for example from CAT, computed axial tomography, data).

As stated, a temporary and/or disposable spacer device, implantable in the human body for the treatment of an infected bone seat or joint seat, comprises a containment body object of the present invention.

The containment body and the possible closing body, if present, must correspond to the external geometry of the spacer to be made, since the outer portion of such a spacer device—and therefore its shape and size—correspond to those of the containment and/or closing body that indeed determine the portion and the outer surface thereof.

According to a version, the setting of the filling material, indeed, conglomerates containment body and possible closing body in a single, solid and rigid structure, to be implanted in the human body.

Such a temporary and/or disposable spacer device, hereafter spacer device, is wholly indicated with reference numeral 13.

The temporary and disposable spacer device 13 comprises an outer portion 14, configured so as to substantially match the shape of the bone seat or of the joint seat with which it must be associated or with part thereof, and an inner portion 15.

In use, the outer portion 14 and the inner portion 15 are constrained to one another.

According to a version, the outer portion comprises a containment body 1, 100, 200.

More specifically, the outer portion 14 corresponds to the containment body 1, 100, 200.

According to another version, the outer portion 14 comprises a containment body 1, 100, 200 and a closing body 9, 109, 209, able to be associated with each other to form a hollow casing.

According to a version of the present invention, the inner portion 15 of the spacer device 13 can comprise at least one filling material of the biologically compatible type, introduced inside the cavity 4, 104, 204 of the containment body 1, 100, 200.

According to a version of the present invention, the filling material can be a liquid or a fluid, more or less viscous, capable of being eluted through the pores 6, 106, 12, 112 respectively present in the containment body 6, 106 and in the closing body 9, 109.

The filling material can comprise at least one pharmaceutical or medical substance to be released through the outer portion 14 of the spacer device 13 that is placed in contact with the bone tissue to be treated.

Preferably, the aforementioned liquid or fluid filling material can be used in a spacer device 13 comprising a containment body 1, 100, 200 with sufficiently thick walls (for example 20 mm), as to give high mechanical strength to the spacer device 13 itself.

According to a further version of the present invention, the filling material can be a liquid or a fluid of the setting or solidifiable type.

In this case, as an example, the filling material can be bone cement.

According to a version, the filling material is prepared by the surgeon, who adds at least one pharmaceutical or medical substance to the components of the filling material.

The use of a setting filling material can be foreseen irrespective of the thickness of the walls of the containment body 1, 100, 200.

According to another version of the present invention, the spacer device 13 can comprise, in the inner portion 15, at least one reinforcing core 16 (illustrated for example in FIG. 6) for the spacer device 13 itself.

According to a further version of the present invention, the inner portion of the spacer device 13 can comprise a plurality of separating walls 7, 107, 207 configured so as to define a substantially trabecular structure, which can be filled or impregnated with at least one pharmaceutical or medical substance.

The at least one separating wall 7, 107, 207 can constitute a single body with the containment body 1, 100, 200; in such a version, the assembly given by at least one separating wall 7, 107, 207 and containment body 1, 100, 200 and possibly closing body 9, 109, 209, and thus form the structure of the spacer device 13.

Figure 8:
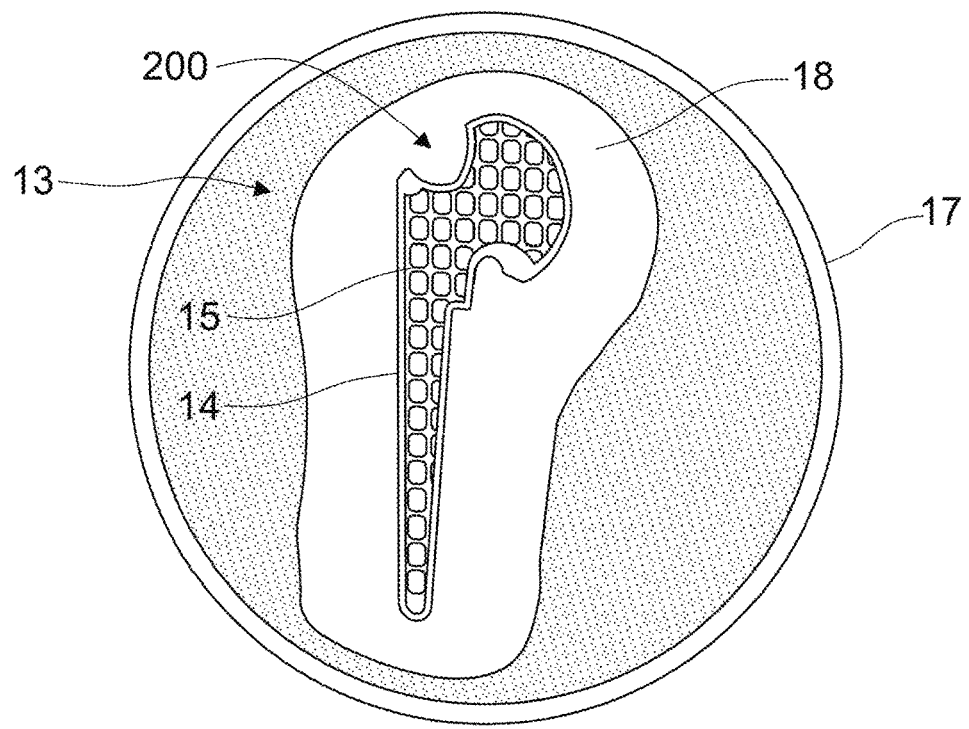
FIG. 8 is a view from above of one half of the temporary and/or disposable spacer device according to FIG. 7 positioned on a Petri dish.

FIG. 8 depicts a section of a spacer device 13 and, in greater detail, a containment body 200, resting on a Petri dish 17.

According to such a version, the outer portion 14 is porous and the inner portion 15 comprises at least one pharmaceutical or medical substance.

On the Petri dish there is a culture of bacteria 18, illustrated as a ring.

As stated, the outer portion 14 of the spacer device 13 is porous and, therefore, the at least one pharmaceutical or medical substance present in the inner portion 15 can come out through the pores of the outer portion 14 thus determining a region 19 inhibiting bacteria growth in the immediate vicinity of the spacer device 13 itself.

According to a further aspect of the present invention, the temporary and disposable spacer device 13 can comprise at least one specific diagnostic or measuring device, not illustrated in the figures, housed inside the containment body 1, 100, 200 or, specifically, inside the at least one cavity 4, 104, 204.

As an example, the spacer device 13 could comprise a biomedical/biological microelectromechanical system, such as a bio-sensor, capable of carrying out chemical-physical detections. Such a bio-sensor, which corresponds to a chip, could comprise a miniaturized circuit in turn comprising an accelerometer and/or a thermometer and/or a load cell and/or sensors suitable for detecting further physical magnitudes of a different type.

The chip to be associated inside a spacer device 13 can be selected as a function of specific requirements of use and of the type of detections to be carried out.

By associating such a chip with the spacer device 13 it is thus possible to detect the conditions of use of the spacer device 13 itself, with reference for example to the accelerations and/or to the loads, static or dynamic, to which it is subjected, to the temperature of the bone seat or joint seat in which it is implanted, etc.

According to a further aspect, the bio-sensor could comprise an integrated interface for transferring the data detected.

As an example, the bio-sensor could comprise data transmission means to allow the detection in real time of the conditions of use of the spacer device 13 with which it is associated.

Hereafter a method for making a temporary and disposable spacer device according to the present invention is described.

The aforementioned method, initially, foresees to provide a containment body 1, 100, 200, shaped so as to be able to be inserted and/or associated with the bone seat or joint seat to be treated or part thereof.

Thereafter, a filling material is introduced, through the opening 5, 105, 205, inside the cavity 4, 104, 204 present in the containment body 1, 100, 200.

As stated, typically, the filling material that can be used is of the solidifiable type, like for example bone cement.

Possibly, during the filling step or in the moments prior to it, at least one bio-sensor can be introduced inside the containment body 1, 100, 200, for detecting the conditions of use of the spacer device 13.

If foreseen, the containment body 1, 100, 200 can be associated with a closing body 9, 109, 209, suitable for closing the opening 5, 105, 205 and therefore the cavity 4, 104, 204.

If foreseen, the at least one bio-sensor is stably constrained inside the containment body 1, 100, 200 following the setting or solidification of the filling material that surrounds it or, if present, by means of the closing body 9, 109, 209 possibly associated with the containment body 1, 100, 200 itself, which prevents it from coming out from the spacer device 13.

When foreseen, the closing body 9, 109, 209 is constrained to the containment body 1, 100, 200 after having filled the at least one cavity 4, 104, 204 with the filling material. In the version in which the filling material is solidifiable, during such solidification, the filling material forms a single body, suitable for being implanted in the human body, together with the containment body 1, 100, 200 and with the closing body 9, 109, 209.

The spacer device 13 is ready for use after setting of the filling material present inside the at least one cavity 4, 104, 204.

According to a version of the present method, it is possible to foresee an insertion step of at least one reinforcing core 16 inside the at least one cavity 4, 104, 204 prior to or after the introduction of the filling material in the cavity 4, 104, 204 itself.

In the case in which constraining means are foreseen, once the filling of the at least one cavity 4, 104, 204 with the filling material is complete, the closing body 9, 109, 209 is constrained to the respective containment body 1, 100, 200.

In accordance with such a version, the inner portion 15 comprises at least one filling material and at least one reinforcing core 16.

As stated, the containment body 1, 100, 200 and the closing body 9, 109, 209 able to be associated with it, are porous.

Therefore, the at least one pharmaceutical or medical substance comprised in the filling material or possibly that contained or impregnated in the containment body 1, 100, 200 and/or in the closing body 9, 109, 209 if present, can be released gradually, and substantially uniformly, through the entire outer surface of the spacer device 13.

According to a further version, the filling material can lack pharmaceutical or medical substances, at least one of which can be impregnated directly in the porosity of the containment body 1, 100, 200 and/or, if foreseen, in the closing body 9, 109, 209, and/or in the filling material.

The containment body 1, 100, 200, possibly associated with the closing body 9, 109, 209, is therefore an integral part of the spacer device 13 and is thus implanted or suitable for being implanted in the human body.

According to such a version, the filling material can be a liquid or a fluid of the solidifiable or non-solidifiable type.

With reference to this last case, the liquid or fluid can be more or less viscous, as a function of the duration of the total treatment period of the infected site, and it can comprise at least one pharmaceutical or medical substance, capable of coming out from the pores 6, 106, 12, 112 present in the outer portion 14 of the spacer device 13. In a version of the invention, the liquid or fluid can have a pasty or gelatinous consistency or in any case such as to be able to stay in the location of insertion, for example without percolating.

The spacer device 13 according to the present invention is capable of ensuring gradual release of at least one pharmaceutical substance even for prolonged periods.

In the inner surface of the containment body and/or of the possible closing body there can be peduncles or extroversions or undercuts (not illustrated) with the function of facilitating the anchoring of the filling material to the walls of the containment body or of the closing body themselves.

The definition given of "porous" element, present in the present description, can be replaced by "semipermeable", without for this reason departing from the scope of protection of the present invention.

The invention thus conceived can undergo numerous modifications and variants all of which are covered by the inventive concept.

The characteristics presented for one version or embodiment can be combined with the characteristics of another version or embodiment, without for this reason departing from the scope of protection of the present invention.

Moreover, all of the details can be replaced with other technically equivalent elements. In practice, the materials used, as well as the contingent shapes and sizes, can be whatever according to requirements without for this reason departing from the scope of protection of the following claims.

The invention claimed is:

1. A method of making a temporary and/or disposable spacer device implantable in a human body for treatment of a bone seat or of a joint seat and adapted to replace an infected prosthesis and provide a substantially uniform release of at least one pharmaceutical or medical substance in the bone seat or joint seat to be treated, the spacer device comprising,
an outer portion, having a shape substantially matching the shape of the bone seat or of the joint seat to be treated or a part of the bone seat or of the joint seat to which the spacer device is to be constrained, and
an inner portion,
the method comprising the steps of:
providing at least one containment body having an outer wall shaped like the bone seat or the joint seat to be treated or a part the bone seat or the joint seat to be treated, so as to constitute an outer portion of the spacer device, and further having a cavity defined by an inner wall of the containment body that is parallel to the outer wall, the cavity having a height, a width, and a depth smaller than at least one of the height or the width of the containment body and further having an open face defined by the height and the width of the containment body, the containment body having a plurality of pores configured so as to place the cavity in communication with an outer environment of the containment body;
providing a filling material;
inserting the filling material in the cavity; and
setting or shaping the filling material, so as to constitute an inner portion of the spacer device,
wherein the filling material and the inner portion so constituted comprises bone cement and the of at least one pharmaceutical or medical substance.

2. The method according to claim 1, wherein the step of setting or shaping the filling material comprises the step of removing an excess of the filling material that protrudes from the containment body.

3. The method according to claim 1, further comprising the step of inserting a reinforcing core inside the at least one containment body.

4. The method according to claim 1, further comprising the step of inserting at least one bio-sensor inside the containment body, for detecting at least one chemical-physical value.

5. The method according to claim 1, further comprising the step of obtaining the temporary and/or disposable spacer device implantable in the human body for the treatment of the bone seat or of the joint seat.

6. The method according to claim 1, wherein the filling material is a liquid, a fluid or a solidifiable liquid or fluid.

7. The method according to claim 1, further comprising the steps of:
providing a separate closing body adapted for closing the open face of the cavity in the containment body, the closing body having a first surface, facing outside the cavity when the closing body is coupled with the containment body, and a second surface opposite the first surface, facing inside the cavity when the closing body is coupled with the containment body; and
coupling the closing body with the containment body so as to define a casing, inside which the inner portion is contained.

8. The method according to claim 7, further comprising the step of constraining the closing body to the containment body through a constraining system.

9. The method according to claim 7, wherein the step of providing a closing body comprises providing the closing body that is porous and has a plurality of pores interconnected with each other, and/or a plurality of pores, and/or at least one through opening, configured so as to place the first surface in communication with the second surface.

10. The method according to claim 7, wherein the containment body and/or the closing body comprises the at least one pharmaceutical or medical substance.

11. The method according to claim 1,
wherein the step of providing at least one containment body comprises providing the at least one containment body having a base portion, and side walls that extend from the base portion, the base portion and the side walls delimiting the cavity therein, and
wherein the base portion and/or at least one of the side walls have at least one through opening, configured so as to place the cavity in communication with the outer environment of the containment body.

12. The method according to claim 11, further comprising the step of accessing to the cavity through the at least one opening delimited by the side walls or by an outer peripheral edge of the side walls, the side walls extending perimetrically from the base portion and/or forming a continuous wall.

13. The method according to claim 11,
further comprising the step of providing at least one separating wall inside the cavity, the at least one separating wall rising up from the base portion and/or from at least one of the side walls, the at least one separating wall defining at least two portions inside a volume of the cavity.

14. The method according to claim 13, wherein there is a plurality of separating walls so as to define a substantially trabecular structure inside the containment body.

\* \* \* \* \*